US010610347B2

(12) United States Patent
Whiting et al.

(10) Patent No.: US 10,610,347 B2
(45) Date of Patent: Apr. 7, 2020

(54) TEXTILE ENGINEERED PROSTHETICS, BIOREACTORS, AND METHODS OF MANUFACTURING TEXTILE ENGINEERED PROSTHETICS

(71) Applicant: THE SECANT GROUP, LLC, Telford, PA (US)

(72) Inventors: Eric H. Whiting, Philadelphia, PA (US); Seth A. Winner, Glenside, PA (US); Emily Y. Ho, Wayne, PA (US); Peter Gabriele, Frisco, TX (US); Jeremy J. Harris, Doylestown, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 385 days.

(21) Appl. No.: 15/074,141

(22) Filed: Mar. 18, 2016

(65) Prior Publication Data

US 2016/0270897 A1  Sep. 22, 2016

Related U.S. Application Data

(60) Provisional application No. 62/135,432, filed on Mar. 19, 2015, provisional application No. 62/147,413, (Continued)

(51) Int. Cl.
*A61F 2/04* (2013.01)
*D03D 3/02* (2006.01)
(Continued)

(52) U.S. Cl.
CPC ............... *A61F 2/04* (2013.01); *A61F 2/062* (2013.01); *C12M 23/34* (2013.01); *C12M 25/02* (2013.01);
(Continued)

(58) Field of Classification Search
CPC .......... D03D 3/02; D03D 3/06; D03D 25/005; D03D 41/004; D03D 11/02;
(Continued)

(56) References Cited

U.S. PATENT DOCUMENTS 3,304,557 A   9/1967 Polansky
5,258,027 A   11/1993 Berghaus
(Continued)

FOREIGN PATENT DOCUMENTS

DE      1541253 A1   10/1969
JP   2002325780 A   11/2002
(Continued)

*Primary Examiner* — Robert H Muromoto, Jr.
(74) *Attorney, Agent, or Firm* — McNees Wallace & Nurick LLC

(57) ABSTRACT

A textile engineered prosthetic includes a continuous tube and at least one band of increased thickness formed over a portion of the continuous tube. The continuous tube includes a body portion and a bifurcated portion. The band of increased thickness forms a biomimetic surface. A bioreactor system includes a bioreactor container including a first compartment, a second compartment, a first membrane separating the first and second compartments, a third compartment, and a second membrane separating the second and third compartments. The bioreactor system also includes a woven textile prosthetic integrated with the bioreactor container in the second compartment to form a single bioreactor unit. A furcated textile article includes a continuous tube having a body portion and a furcated portion bifurcated N times from the body portion. The furcated textile article is a continuous woven piece formed from N shuttles of a shuttle loom, where N is at least two.

13 Claims, 12 Drawing Sheets

Related U.S. Application Data filed on Apr. 14, 2015, provisional application No. 62/160,955, filed on May 13, 2015.

(51) Int. Cl.
*A61F 2/06* (2013.01)
*C12M 1/00* (2006.01)
*C12M 1/12* (2006.01)
*A61F 2/90* (2013.01)

(52) U.S. Cl.
CPC ............... *C12M 25/14* (2013.01); *D03D 3/02* (2013.01); *A61F 2002/046* (2013.01); *A61F 2230/006* (2013.01); *A61F 2240/001* (2013.01); *A61F 2250/0026* (2013.01); *A61F 2250/0036* (2013.01); *D10B 2509/06* (2013.01)

(58) Field of Classification Search
CPC ...... A61F 2230/0067; A61F 2/06; A61F 2/04; A61F 2002/046; A61F 2230/006; A61F 2240/001; A61F 2250/0026; A61F 2250/0036; A61F 2/07
See application file for complete search history.

(56) References Cited

U.S. PATENT DOCUMENTS

| | | | |
|---|---|---|---|
| 5,605,835 A | 2/1997 | Hu et al. | |
| 5,824,040 A * | 10/1998 | Cox | A61F 2/07 606/194 |
| 6,283,991 B1 * | 9/2001 | Cox | A61F 2/07 623/1.13 |
| 9,216,100 B2 * | 12/2015 | Seibold | A61F 2/90 |
| 9,492,268 B2 * | 11/2016 | Winner | D03D 3/02 |
| 9,827,086 B2 * | 11/2017 | Winner | A61F 2/06 |
| 2005/0273155 A1 | 12/2005 | Bahler et al. | |
| 2006/0030926 A1 * | 2/2006 | Berra | A61F 2/06 623/1.13 |
| 2006/0141607 A1 | 6/2006 | Wikswo et al. | |
| 2008/0090292 A1 * | 4/2008 | Brooks | C12N 5/0653 435/395 |
| 2008/0183248 A1 * | 7/2008 | Rezai | A61N 1/0553 607/62 |
| 2008/0195189 A1 * | 8/2008 | Asgari | A61F 2/82 623/1.2 |
| 2010/0249902 A1 * | 9/2010 | Sakai | A61F 2/07 623/1.16 |
| 2012/0116492 A1 * | 5/2012 | Seibold | A61F 2/07 623/1.11 |
| 2014/0135906 A1 * | 5/2014 | Winner | D03D 3/02 623/1.51 |
| 2015/0320542 A1 * | 11/2015 | Gabriele | A61L 31/06 623/1.13 |
| 2015/0342721 A1 * | 12/2015 | Winner | D03D 3/02 623/1.51 |
| 2016/0270897 A1 * | 9/2016 | Whiting | A61F 2/04 |
| 2016/0305050 A1 * | 10/2016 | Winner | D03D 41/004 |

FOREIGN PATENT DOCUMENTS

| | | |
|---|---|---|
| WO | 2005047466 A2 | 5/2005 |
| WO | 2007021919 A1 | 2/2007 |

* cited by examiner

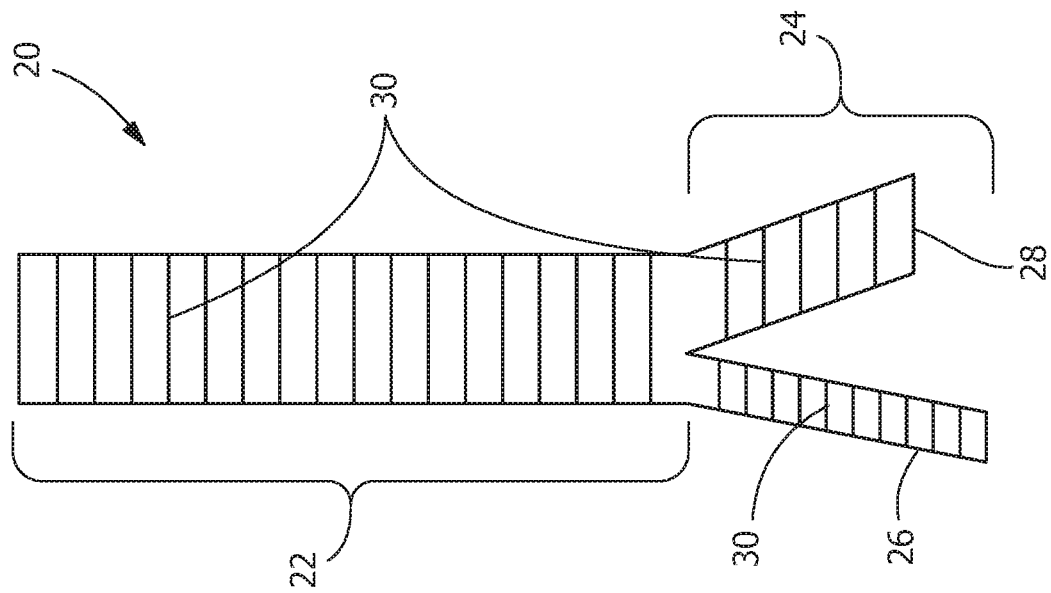
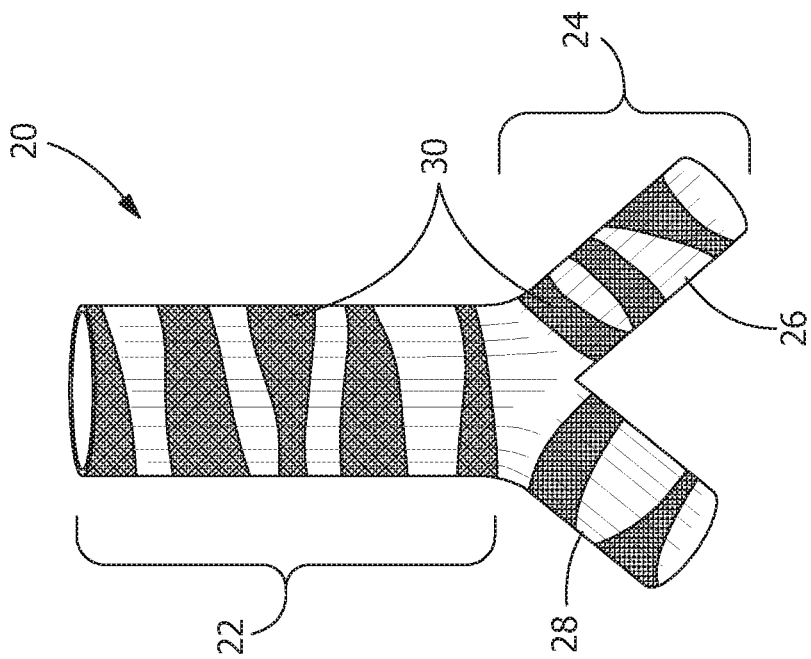

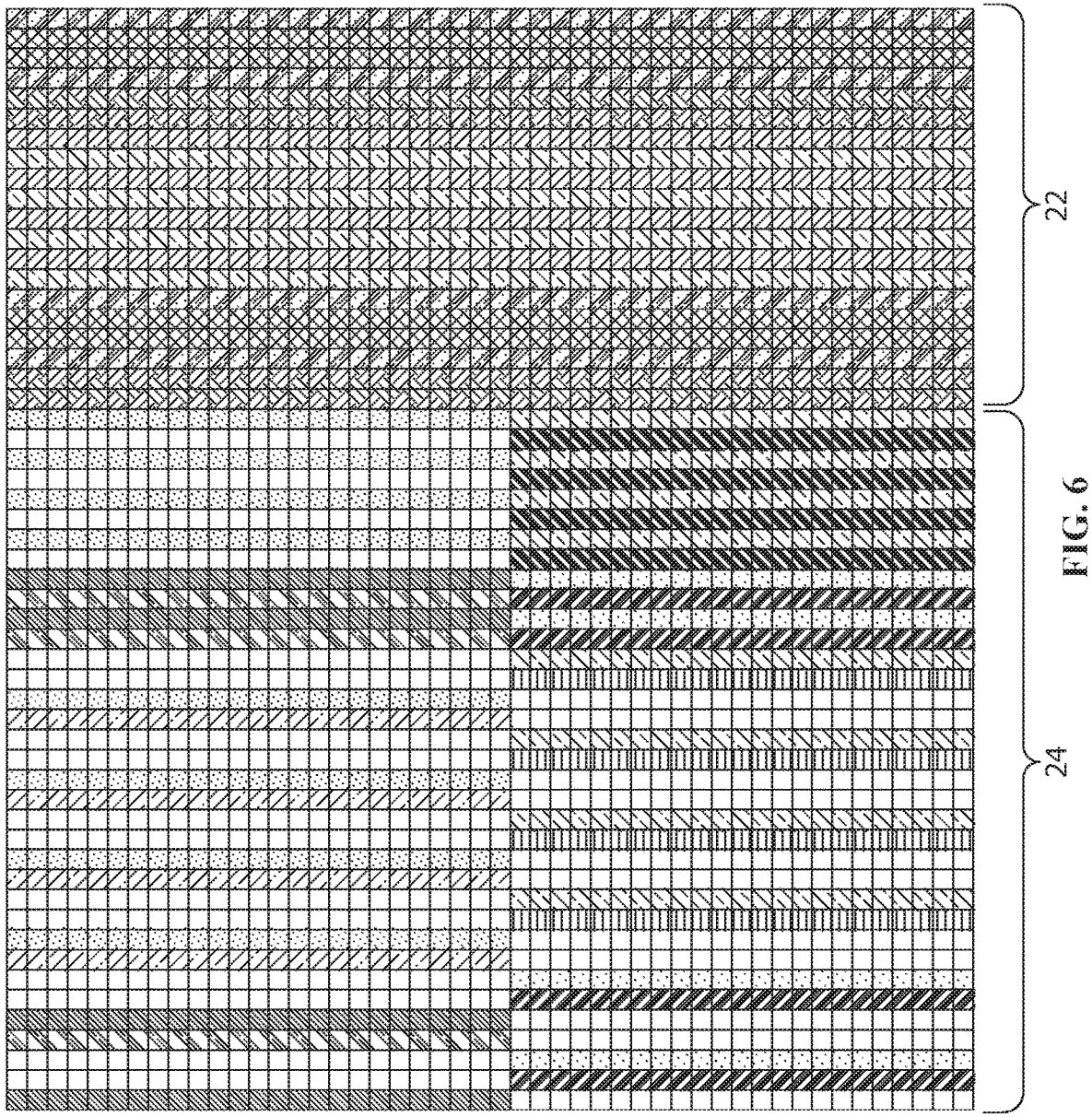

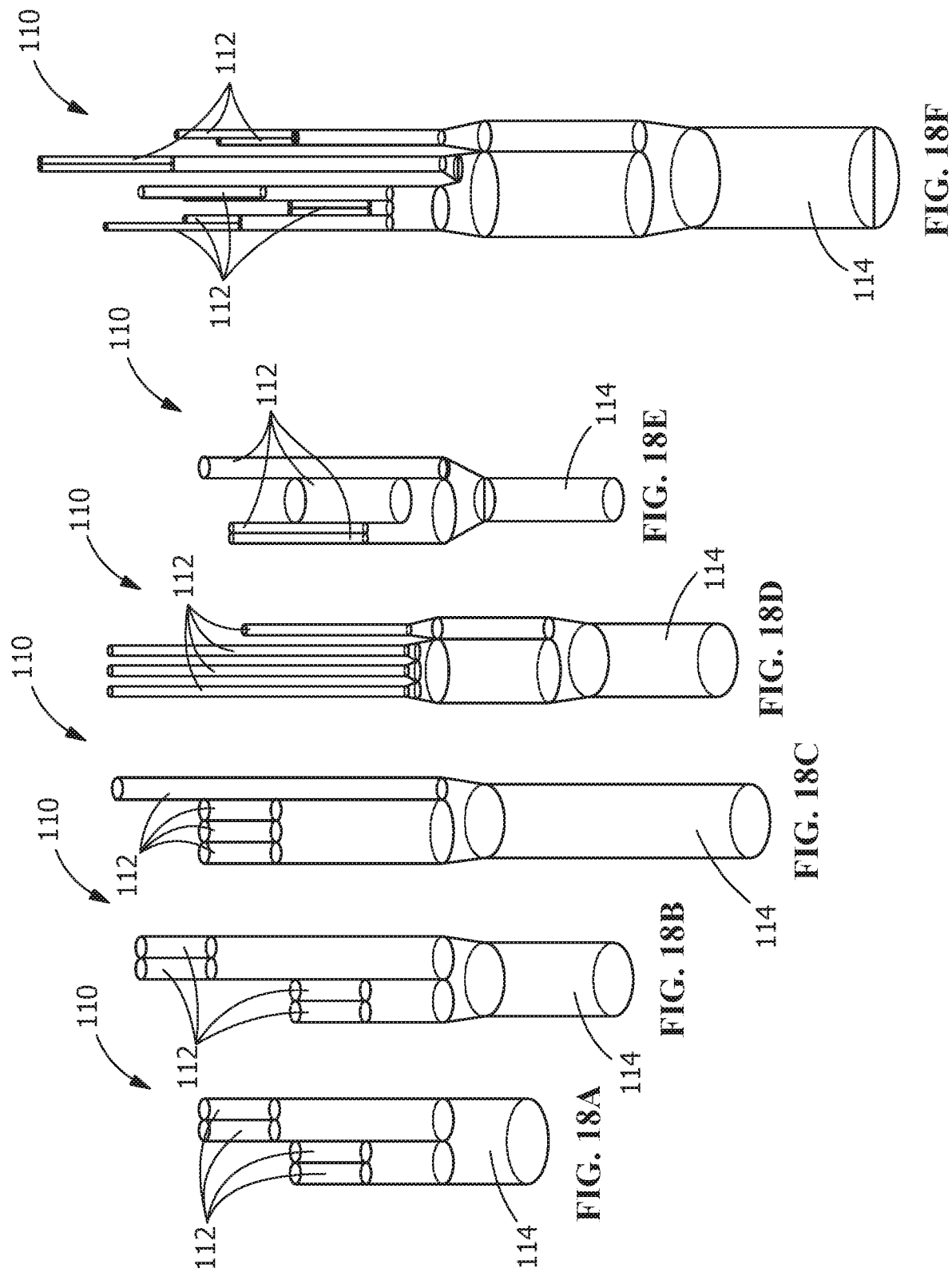

TEXTILE ENGINEERED PROSTHETICS, BIOREACTORS, AND METHODS OF MANUFACTURING TEXTILE ENGINEERED PROSTHETICS

CROSS-REFERENCE TO RELATED APPLICATIONS

This application claims priority to and the benefit of U.S. Provisional Application No. 62/135,432 filed Mar. 19, 2015, U.S. Provisional Application No. 62/147,413 filed Apr. 14, 2015, and U.S. Provisional Application No. 62/160,955 filed May 13, 2015, which are hereby incorporated by reference in their entirety herein.

FIELD OF THE INVENTION

This application is directed to textile engineered prosthetics, bioreactors, and methods of making textile engineered prosthetics. More particularly, the present application is directed to textile engineered prosthetic tracheas, textile engineered prosthetic vascular grafts, bioreactor containers for prosthetics, and methods of making the same.

BACKGROUND OF THE INVENTION

Prosthetic devices have many different applications in medicine.

The trachea is a tube that extends from the larynx to the lungs, and allows the passage of air therethrough. Depending on the individual, the trachea usually includes between fifteen and twenty incomplete, C-shaped cartilaginous rings. The cartilaginous rings reinforce the anterior and lateral sides of the trachea to protect and maintain the airway while leaving a dorsal side of the trachea devoid of cartilaginous rings. The incomplete structure of the cartilaginous rings allows the trachea to collapse slightly as food passes through the esophagus, which lies posterior to the trachea. Additionally, a trachealis muscle connects the ends of the incomplete rings and contracts during coughing, reducing the size of the lumen of the trachea.

For various reasons, such as injury, tumor, and/or infection, it may be necessary to reconstitute at least a portion of the trachea. Often, reconstituting the trachea includes direct anastomosis through use of an artificial trachea, or trachea replacement constructed of an artificial material. Current artificial trachea technologies generally include electrospinning, molded forms, and other non-wovens. However, these technologies typically do not provide suitable biomimetic structures. For example, an artificial trachea formed through electrospinning may not include anatomically correct bifurcation of the right and left bronchial branches or cartilaginous rings. Additionally, electrospun artificial tracheas are often rigid, causing patients to experience pain and/or difficulty during ambulation and/or swallowing after implantation.

These and other drawbacks are associated with current coated products and methods used for forming coated products.

Vascular aneurysms are an abnormal dilation that can occur in the aorta or any other blood vessels, with more predominance in arterial blood vessels than veins. Vascular aneurysms are serious and dangerous medical conditions that typically necessitate surgical repair. The repair involves implantation of a graft within the blood vessel.

The aneurysm often extends into areas of bifurcation, such as where a large artery splits into two smaller branch vessels. While bifurcated grafts have been common for some time, some vascular repair surgeries are more extensive, for which tri-furcated or quadfurcated grafts are desirable.

While grafts having three or four furcations have been proposed, they have not yet come into wide use. A primary drawback of current versions of such grafts is that it is necessary to sew or adhere together multiple bifurcated grafts to achieve higher furcations. Sewing multiple grafts in situ is time consuming and creates potential for blood turbulence and possibly even leakage at the seam where the grafts are sewn together.

These and other drawbacks are associated with current grafts having more than two furcations.

BRIEF DESCRIPTION OF THE INVENTION

Exemplary embodiments are directed to a textile engineered prosthetic, bioreactors, and methods of making a textile engineered prosthetic.

According to an exemplary embodiment, a textile engineered prosthetic includes a continuous tube and at least one band of increased thickness formed over a portion of the continuous tube. The continuous tube includes a body portion and a bifurcated portion extending from the body portion. The at least one band of increased thickness forms a biomimetic surface.

According to another exemplary embodiment, a method of manufacturing a textile engineered prosthetic includes forming a continuous tube and forming at least one band of increased thickness over a portion of the continuous tube. The forming of the band of increased thickness provides a biomimetic surface.

According to another exemplary embodiment, a bioreactor system includes a bioreactor container including a first compartment, a second compartment, a first membrane separating the first compartment from the second compartment, a third compartment, and a second membrane separating the second compartment from the third compartment. The bioreactor system also includes a regenerative scaffold integrated with the bioreactor container in the second compartment to form a single bioreactor unit.

According to another exemplary embodiment, a furcated textile article includes a continuous tube having a body portion and a furcated portion bifurcated N times from the body portion. The furcated textile article is a continuous woven piece formed from N shuttles of a shuttle loom, where N is at least two.

According to another exemplary embodiment, a method of manufacturing a furcated textile article includes weaving a continuous tube with a shuttle loom and furcating the continuous tube into N portions. N is at least two, and N is equal to a shuttle capacity of the shuttle loom.

Among the advantages of exemplary embodiments is that methods described herein produce a textile engineered prosthetic having an improved anatomical shape as compared to existing prosthetics.

Another advantage is that the methods may produce bifurcated branches having different diameters.

Still another advantage is that the methods produce prosthetics having improved biomimetic surfaces.

A further advantage is that the methods provide a prosthetic trachea having C-shaped bands of increased thickness for replacing cartilaginous rings and a compliant portion providing room for the esophagus.

Another advantage is that the methods produce an implantable device having materials and/or fibers for multi-structured organ development, tissue culture, or emergency use.

Exemplary embodiments are directed to woven textile prosthetics having three, four, or even more complex graft divisions as a single unit.

Thus, exemplary embodiments are directed to vascular grafts and other textile prostheses that are woven to a near-net shape. In some embodiments, the near-net shape woven textiles are placed over a sewing mandrel and have shape memory stent material sewn to the outside to give the fabric form its final shape, in situ.

Among the advantages of exemplary embodiments is that because the prosthesis is woven as a unitary structure in its complete form, there are few or no seams to impede blood flow or create turbulence.

Another advantage is that exemplary embodiments allow for a seamless sidewall for blood flow when used in vascular graft surgery and avoid the drawbacks associated with current methods of multi-furcated graft structures.

Another advantage is that the methods may be used to produce multiple branches having different diameters.

Another advantage is that the methods produce an implantable device having materials and/or fibers for multi-structured organ development, tissue culture, or emergency use.

Other features and advantages of the present invention will be apparent from the following more detailed description of exemplary embodiments that illustrate, by way of example, the principles of the invention.

BRIEF DESCRIPTION OF THE DRAWINGS

FIG. 1 schematically shows a front view of a textile engineered prosthetic trachea having anatomical sections of increased thickness in an embodiment of the present disclosure.

FIG. 2 schematically shows a front view of a textile engineered prosthetic trachea having general sections of increased thickness in an embodiment of the present disclosure.

FIG. 6 schematically shows a portion of a shuttle sequence for forming a bifurcation in a textile engineered prosthetic trachea in an embodiment of the present disclosure.

FIG. 18A schematically shows another of quadfurcated vascular graft design in an embodiment of the present disclosure.

FIG. 18B schematically shows another quadfurcated vascular graft design in an embodiment of the present disclosure.

FIG. 18C schematically shows another quadfurcated vascular graft design in an embodiment of the present disclosure.

FIG. 18D schematically shows another quadfurcated vascular graft design in an embodiment of the present disclosure.

FIG. 18E schematically shows another quadfurcated vascular graft design in an embodiment of the present disclosure.

FIG. 18F schematically shows a 10-furcated vascular graft design in an embodiment of the present disclosure.

Wherever possible, the same reference numbers will be used throughout the drawings to represent the same parts.

DETAILED DESCRIPTION OF EXEMPLARY EMBODIMENTS

Exemplary embodiments are directed to textile engineered prosthetics, bioreactor systems, and methods of making textile engineered prosthetics. Embodiments of the present disclosure, in comparison to prosthetics and methods not using one or more of the features disclosed herein, provide improved anatomical shapes as compared to existing prosthetics, produce anatomically correct bifurcations, produce bifurcations having differing geometries, produce prosthetics having improved biomimetic surfaces, and combinations thereof.

Provided herein are a textile engineered prosthetic and a method of forming the textile engineered prosthetic for human use and/or other animal use. In one embodiment, the textile engineered prosthetic includes a woven prosthetic. In another embodiment, the woven prosthetic includes a prosthetic trachea having a net or near-net shape. Although discussed primarily with respect to a prosthetic trachea, as will be appreciated by those skilled in the art, the textile engineered prosthetic may form other organs in the body, such as, but not limited to, an intestinal prosthetic device, a bronchial tree, an esophagus, artificial blood vessels, other dimensionally pulsating surfaces, or a combination thereof.

The woven prosthetic includes any resorbable material, non-resorbable material, or combination of materials suitable for weaving. Suitable non-resorbable materials include, but are not limited to, polyethylene terephthalate (PET), silicone, polyurethane, polycarbonate, polyether ketone, or a combination thereof. Suitable resorbable materials include, but are not limited to, polycaprolactone (PCL), polylactic acid (PLA), polyglycolic acid (PGA), poly(glycerol sebacate) (PGS), or a combination thereof. Additionally or alternatively, the woven prosthetic may include natural polymer fibers such as, but not limited to, collagen, fibronectin, hyaluronic acid, or a combination thereof. In another embodiment, a ratio of materials is selected to provide predetermined tissue compliance and/or biological properties. Based upon the material used to form the woven structure, the textile engineered prosthetic forms permanent hardware for a patient or an article of regenerative medicine. For example, permanent hardware may include non-resorbable materials or combinations of resorbable and non-resorbable materials, while articles of regenerative medicine may include scaffolds formed from resorbable materials which are broken down after implantation.

Figure 3:
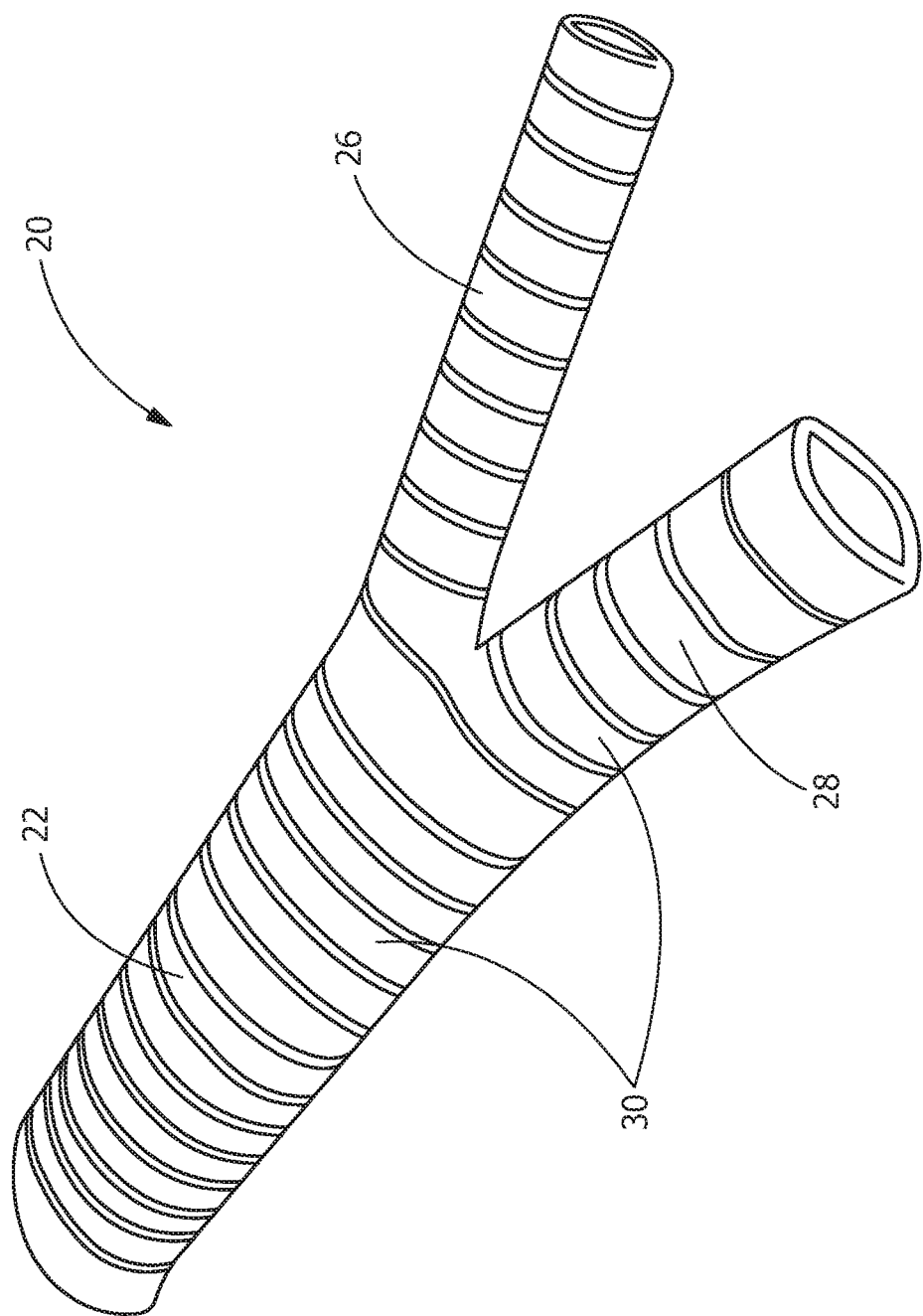
FIG. 3 shows a perspective view of a textile engineered prosthetic trachea formed according to an embodiment of the present disclosure.

In one embodiment, the net or near-net shape of the prosthetic trachea corresponds to the anatomical shape of a trachea or any portion thereof. For example, as illustrated in FIGS. 1-3, the prosthetic trachea 20 includes a body portion 22 having a bifurcated portion 24 extending therefrom. The body portion 22 forms a single lumen, which corresponds to the trachea, that transitions into two separate lumens 26, 28 at the bifurcated portion 24, which correspond to the right bronchial and left bronchial branches. As will be appreciated by those skilled in the art, although shown as including both the body portion 22 and the bifurcated portion 24, the prosthetic trachea 20 may include any individual section or portion thereof.

The separate lumens 26, 28 formed by the bifurcated portion 24 each include any suitable size, shape, and/or orientation. For example, each of the lumens 26, 28 may include a different length and/or diameter corresponding to an anatomically correct bifurcated shape of the right and left bronchial branches. Additionally, the size, shape, and/or orientation of any portion of the prosthetic trachea 20 may be adjusted during manufacturing based upon the actual anatomical shape of the trachea being reconstituted.

In some embodiments, the body portion 22 includes 16-20 bands 30 of increased thickness corresponding to the cartilaginous rings in a human trachea, has a width of about 0.75 to one inch, and has a length of about 4 to 5 inches, alternatively about 4.5 inches. In some embodiments, the first lumen 26 corresponds to the left bronchi, includes 9-12 bands 30 of increased thickness corresponding to the cartilaginous rings in a human trachea, has a width of about 0.3 to 0.4 inches, alternatively about 0.34 inches, and has a length of about 1.75 to 2.25 inches, alternatively about 2 inches. In some embodiments, the second lumen 28 corresponds to the right bronchi, includes 6-8 bands 30 of increased thickness corresponding to the cartilaginous rings in a human trachea, has a width of about 0.6 to 0.75 inches, alternatively about 0.66 inches, and has a length of about 1.25 to 1.75 inches, alternatively about 1.5 inches.

In some embodiments, a method of making the textile engineered prosthetic 20 includes weaving multiple layers to form a net or near-net shape woven structure. In some embodiments, the method includes providing a tubular construction having a face fabric and a back fabric, and joining the face fabric and the back fabric with movement of a fill material, such as yarn, from the face to the back of the fabric. In a further embodiment, the weaving includes a jacquard weaving process. The jacquard weaving process facilitates control between the structural relationship of the horizontal and vertical intersections of warp and fill yarn, with a predetermined quill placement controlling the fill material being thrown across the shed.

A woven draft of the design may be provided to specify textile structures, shuttle movements, and/or pick count densities for the making of the textile engineered prosthetic. Varying the textile structures, shuttle movements, and/or pick count densities throughout the weaving forms variations on and/or within one or more portions of the prosthetic. Suitable variations include, but are not limited to, variations in thickness, dimension, geometry, texture, elasticity, other material properties, or a combination thereof.

Figure 4:
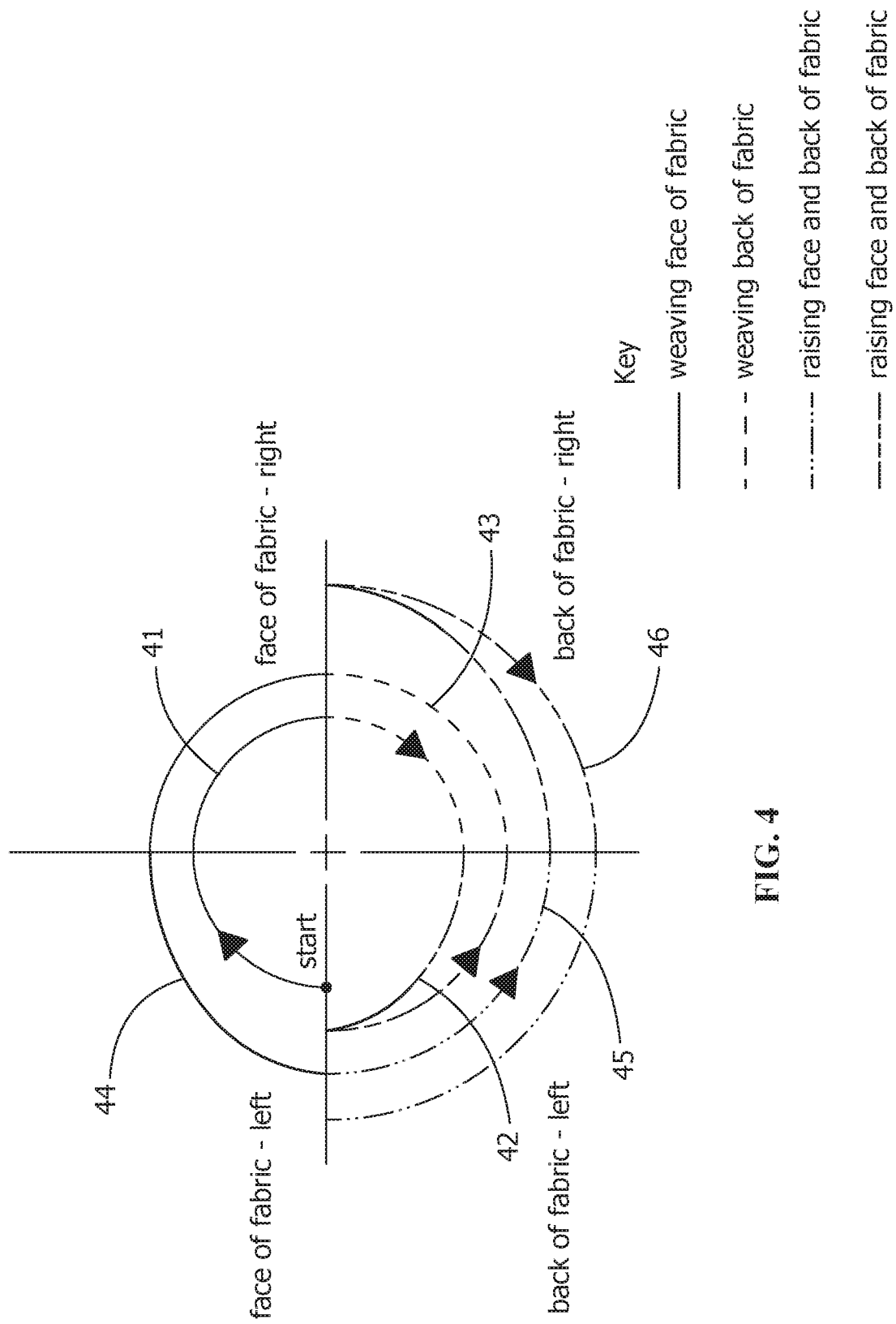
FIG. 4 shows a lined schematic view of a weaving process for forming a textile engineered prosthetic trachea in an embodiment of the present disclosure.
Figure 5:
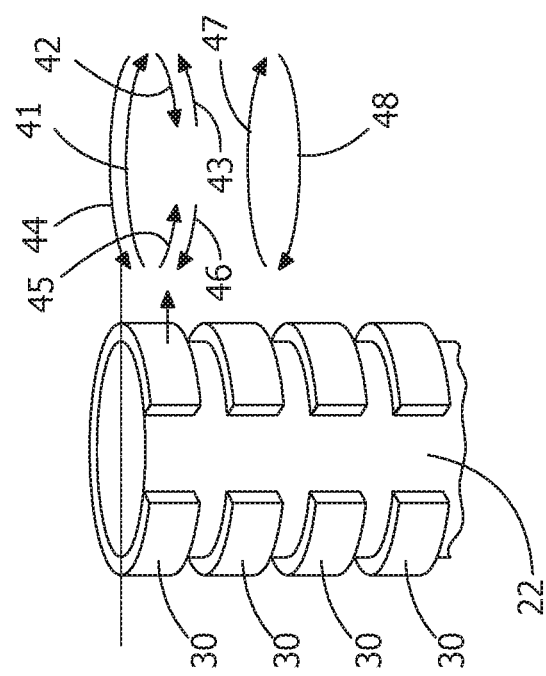
FIG. 5 shows a numbered schematic view of a weaving process for forming a textile engineered prosthetic trachea in an embodiment of the present disclosure.

For example, referring to FIGS. 1-3, in one embodiment, the method includes forming a continuous tube shape having one or more bands 30 of increased thickness on an outer surface thereof. As illustrated in FIGS. 4-5, in another embodiment, the bands of increased thickness are formed in a six-step shuttle motion. Starting from the face of the fabric weavers left, the sequence of the six-step shuttle motion includes (i) moving from face of the fabric left to face of the fabric right to weave a face of the fabric (step 41); (ii) moving from face of the fabric right to back of the fabric left to weave a back fabric right (step 42); (iii) moving from back of the fabric left to back of the fabric right to weave the back fabric right (step 43); (iv) moving from back of the fabric right to face of the fabric left to weave the face of the fabric (step 44); (v) moving from face of the fabric left to back of the fabric right to weave a back fabric left (step 45); and (vi) moving from back of the fabric right to back of the fabric left to weave the back fabric left (step 46). The six-step sequence is illustrated diagrammatically in FIG. 6, which shows a diagram of patterns of a portion of the sequence, where the body portion 22 transitions to the bifurcated portion 24. The plain white squares in FIG. 6 represent a "miss". As shown in FIG. 5, an additional two motions (steps 47 and 48), preferably with PET, form the remaining section that is not of increased thickness corresponding to the band 30 section.

During the six-step shuttle motion, the face of the fabric is raised when weaving the back of the fabric. Before returning to the face of the fabric, two passes are made to a dedicated back side of the fabric, which includes a left part, a middle part, and a right part. When weaving the right part, the left part and the middle part are raised. When weaving the left part, the right part and the middle part are raised.

The six-step shuttle motion facilitates formation of the bands 30 of increased thickness, which correspond to the cartilaginous rings in a human trachea and provides a biomimetic surface on the prosthetic. In one embodiment, the bands 30 of increased thickness include a similar or substantially similar shape and/or mechanical property as the cartilaginous rings. In another embodiment, the bands 30 of increased thickness are formed from PGS porogen derived technologies. The bands 30 of increased thickness extend around at least a portion of the prosthetic trachea and/or include any suitable geometrical shape along a length of the prosthetic. For example, the bands 30 of increased thickness may extend around between ⅕ and ⅘, between ¼ and ¾, and/or between ⅓ and ⅔ of an outer diameter of the prosthetic to mimic the C-shaped cartilaginous rings. Additionally, the geometric shape of the sections may be varied (see FIG. 1), uniform, and/or substantially uniform (see FIG. 2) along a length of the prosthetic. In a further embodiment, the bands 30 of increased thickness are hollow or substantially hollow to facilitate a filling of the bands 30. The bands 30 may be filled with any material suitable for adjusting various properties of the bands 30, such as, but not limited to, strength, stability, rigidity, any other mechanical property, or a combination thereof. For example, the bands 30 may be filled with a rigid material, an injected silicone, and/or a three-dimensionally printed form.

The continuous tube between and behind the bands 30 of increased thickness provides a flexibility in the prosthetic, facilitating bending and/or other movement. For example, in one embodiment, the portions of the continuous tube positioned between the bands 30 of increased thickness provide a decreased rigidity as compared to the bands 30 of increased thickness, which facilitates bending of the prosthetic. In another embodiment, the portions of the continuous tube exposed where the bands 30 of increased thickness are circumferentially disconnected provide a compliant surface. The compliant surface facilitates movement within the prosthetic, including, for example, movement corresponding to physiological changes in adjacent body parts such as the esophagus during swallowing.

The six-step shuttle motion also facilitates formation of an anatomically correct bifurcation of right and left bronchial branches, providing the net or near-net shape of the prosthetic. In one embodiment, the bifurcation forms two tubes having different diameters and/or lengths. For example, the right tube may have a larger diameter than the left tube, while the left tube has a longer length than the right tube. In another embodiment, the prosthetic trachea is formed using four shuttles, with shuttle one (s1) and shuttle four (s4) weaving the weavers right tube, and shuttle two (s2) and shuttle three (s3) weaving the weavers left tube. In a further embodiment, forming the bifurcation includes weaving in a multi-step FIG. 8 motion between the right and left bronchial tubes. The weaving of the bifurcation includes two picks of the left bronchi while the right bronchi is all down, followed by two picks of the right bronchi while the left bronchi is all down.

In one embodiment, the prosthetic including the bands 30 of increased thickness has eight woven structures. The eight woven structures include two on the face, two on the tube face, two on the tube back, and two on the back. The tube face and the tube back form the continuous tube between and behind the bands 30 of increased thickness. The face of the band 30 of increased thickness creates a channel between itself and the tube face around the circumference of the prosthetic, forming the bands 30 as hollow or substantially hollow. The multiple structures of the face, the tube face, the tube back, and/or the back are joined together through movement of warp yarns from the face of the fabric to the back of the fabric during a face pick of the specific structure; or vice versa. In another embodiment, a combination of multiple woven structures facilitates control of density and/or surface texture across both the outside and the inside of the prosthetic during manufacturing.

Figure 7:
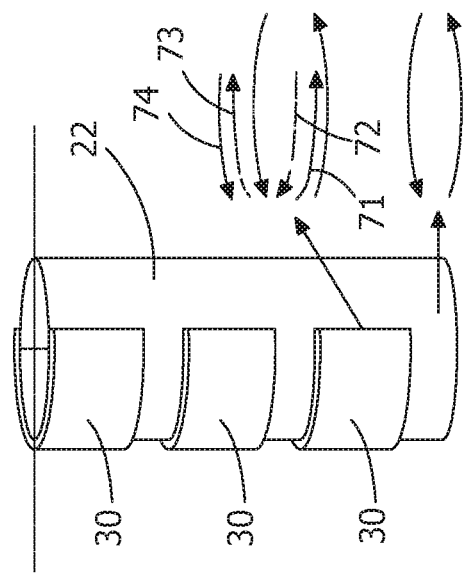
FIG. 7 shows a schematic view of an alternate shuttle sequence for forming a textile engineered prosthetic trachea in an embodiment of the present disclosure.

Alternate methods of making the textile engineered prosthetic 20 include embroidering the bands 30 of increased thickness on the continuous tube, forming the tube and/or bands 30 of increased thickness through weaving processes having different shuttle sequences, or a combination thereof. For example, as illustrated in FIG. 7, one alternate method includes a four-step shuttle motion for forming straight portions of the prosthetic having the bands 30 of increased thickness. Starting from face of the fabric weavers left, the four-step shuttle motion includes (i) moving from face of the fabric left to face of the fabric right to weave a face of the fabric (step 71); (ii) moving from face of the fabric right to face of the fabric left to weave the face of the fabric (step 72); (iii) moving from face of the fabric left to back of the fabric right to weave a back of the fabric (step 73); and (iv) moving from back of the fabric right to back of the fabric left to weave the back of the fabric (step 74). During the four-step shuttle motion, the face of the fabric is raised when weaving the back of the fabric. The face and the back are each divided into two portions, portion A and portion B. Portion A includes ⅔ of the fabric and portion B includes the remaining ⅓ of the fabric. When portion A is located on weavers left, the orientation will be maintained for both the face of the fabric and the back of the fabric, with portion A being denoted as the woven area. Although this four-step shuttle motion is faster than the previously-described six-step shuttle motion, it does not allow for bifurcation.

In one embodiment, the textile engineered prosthetic includes an additive and/or coating. In another embodiment, the additive and/or coating may include an elastomer or bioelastomeric resin, such as, but not limited to, PGS. For example, the prosthetic may include fibers formed from the elastomer and/or be coated with the elastomer. In a further embodiment, the elastomer adjusts the structural properties of the prosthetic, facilitates enhanced cell colonization, maintains a shape of the prosthetic, provides controlled release of an element or composition, or a combination thereof. The elastomer may also be molded and/or embossed to provide topological and/or spatial surface features on the prosthetic.

Additionally or alternatively, the prosthetic is seeded or incubated with biological cells and/or release agents. Suitable release agents include, for example, trophic agents; proteins; peptides; cell growth agents; filler oxides; compounds that promote cellular attachment, cellular differentiation, regeneration, and/or tissue colonization; or a combination thereof. The release agents are released through any suitable release method, such as, but not limited to, coating release, controlled coating release, fiber degradation, or a combination thereof. For example, the prosthetic may be formed from degradable fibers including filler oxides or other release agents that are released as the fibers degrade. Suitable biological cells include, but are not limited to, progenitor cells, autologous cells, allogenic cells, mesenchymal progenitor cells, stem cells, or a combination thereof. The progenitor cells and/or release agents facilitate integration of the prosthetic and/or prosthetic functioning similar or substantially similar to that of the biological organ being reconstituted and/or replaced.

In one embodiment, after exposure of the prosthetic to the biological cells and/or the release agents, the prosthetic is incubated in a bioreactor prior to implantation. In another embodiment, the prosthetic includes additives, such as, but not limited to, fluorescence compounds, radio opaque compounds, anti-bacterial compounds, growth hormones, conductive compounds, ceramic compounds, metallic compounds, oxygen sensing compounds, radioactive compounds, hormones, cytokines, or combinations thereof. In a further embodiment, the prosthetic includes addition anatomical and non-anatomical features such as, for example, a feature configured to facilitate post-surgical tracheotomy, pores, dimples, hairs, patterned embossing, or a combination thereof.

The textile engineered prosthetic formed according to one or more of the embodiments disclosed herein provides an increased level of anatomical design flexibility as compared to existing prosthetics. The anatomical design flexibility facilitates controlled dimensional variability corresponding to biological differences, such as the inherent differences between individuals of the same sex (e.g., between males or between females), and/or between individuals of different sexes (e.g., between males and females). For example, adjusting the scale of the prosthetic according to one or more of the methods disclosed herein provides anatomical flexibility corresponding to individuals of various sizes. A continuity provided by applying the same weaves maintains the mechanical properties of the prosthetic at each scale.

The textile engineered prosthetic may also include fiber combinations that provide tissue-specific fiber chemistry through the weaving techniques disclosed herein and/or the use of gradient or hybrid fiber architecture. The fibers may also be functionalized or include an external architecture to facilitate contour guidance, cellular colonization, and/or cellular migration through at least a portion of the prosthetic.

In one embodiment, the method of making the textile engineered prosthetic includes forming multiple small diameter bifurcations. In another embodiment, the multiple small diameter bifurcations are attached to the right and/or left bronchial tubes through a post-processing treatment. The attachment of the small diameter bifurcations facilitates extension of the bronchial tree formed according to one or more of the methods disclosed herein. Additionally or alternatively, the method may include weaving a gauze membrane having a bifurcated form corresponding to the protective fibrous membrane surrounding and protecting a biological trachea. The gauze membrane may be attached to the prosthetic trachea formed according to one or more of the methods disclosed herein through a post-processing treatment.

The invention is further described in the context of the following example which is presented by way of illustration, not of limitation. In the example, the method was carried out in accordance with one or more of the embodiments disclosed herein.

In one example, a prosthetic trachea was formed with a jacquard loom using a four shuttle batten and an 80 ton loom pick wheel. The jacquard loom included a total of 1200 ends combined together to create a woven tube having an on loom flat width of about 1.5 inches. Prior to starting the weaving process, the shuttles were arranged with s1, s2, and s3 on weavers left, and s4 on weavers right. A predetermined quill placement was used to control the fill material being thrown across the shed, and included a placement of s1: PET—40D; s2: PET mono—0.008; s3: PET mono—0.008; and s4: PET—40D.

Figure 8:
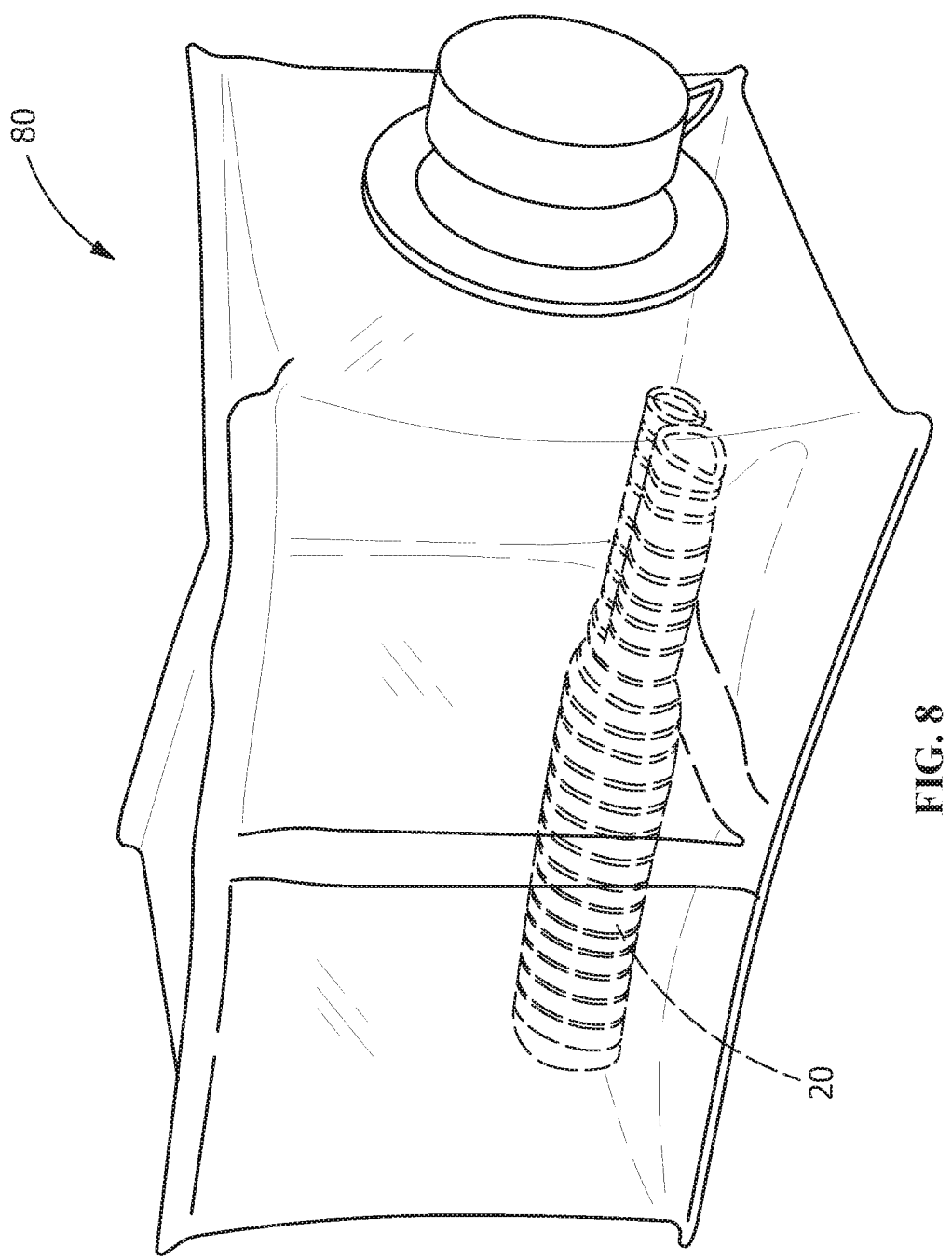
FIG. 8 schematically shows a textile engineered prosthetic trachea in a bioreactor container in an embodiment of the present disclosure.

According to yet another embodiment, the engineered textile prosthetic trachea 20 may be integrated within a bioreactor container 80 such that the bioreactor container 80 and the prosthetic trachea 20 are part of a single, individualized unit as shown in FIG. 8 that provides an off-the-shelf, yet still full customizable, tissue scaffold. Following manufacture, the textile prosthetic trachea 20 may be placed within the bioreactor container 80 to form the integrated system upon closure of the bioreactor container 80. Although a prosthetic trachea 20 is shown in FIG. 8, any scaffold to promote regenerative growth may be placed within the bioreactor container 80 within the spirit of the present disclosure. Exemplary scaffolds include textiles, as well as those formed by molding, electro-spinning, or additive manufacturing into a pre-determined structure. Textile scaffolds may be woven but can also be formed by any other technique, including, for example, braided, knit, and non-woven textiles.

Within the bioreactor container 80, a serum or other fluid containing cells for initiating growth on the prosthetic/scaffold and/or pharmaceutical ingredients or other drugs for enhancing acceptance by the body upon transplant. These other materials may be placed in the container together with the prosthetic trachea 20 in a single compartment initially or, may be divided into one or more separate compartments for subsequent combination at a predetermined point prior to use.

Figure 9:
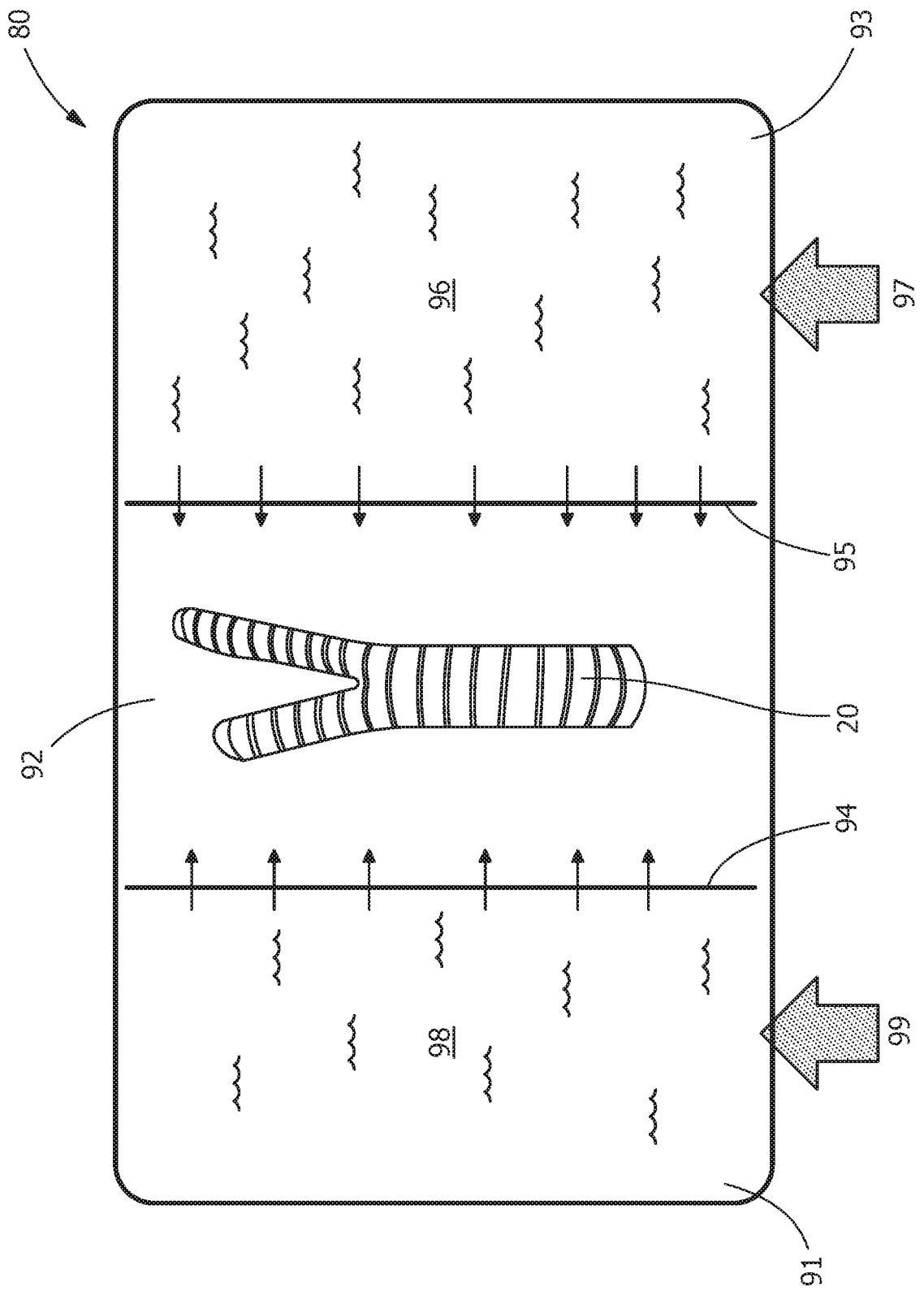
FIG. 9 schematically shows a three compartment bioreactor container containing the textile engineered prosthetic trachea in an embodiment of the present disclosure.

For example, referring to FIG. 9, a bioreactor container 80 that is multi-compartmental is schematically illustrated in cross-section with three compartments 91, 92, 93 separated from one another by diffusion membranes 94, 95. A buffer solution 98 is preloaded in the first compartment 91 for drug 99 compounding, the prosthetic trachea 20 resides in the middle compartment 92, and the third compartment 93 contains a suitable bio-fluid 96 compatible for cells 97 and/or growth factors. Once the prosthetic trachea 20 is exposed to the bio-fluid 96 and buffer solution 98, the prosthetic trachea 20 has a short shelf life before it must be implanted, so the bioreactor container 80 keeps the components separate until the appropriate times prior to implantation.

At one point prior to the surgery during which the prosthetic trachea 20 is to be implanted, typically several days in advance to permit sufficient time for growth, cells 97 are injected into the bio-fluid 96 of the third compartment 93. The membrane 95 separating that compartment 96 and the prosthetic trachea 20 is then compromised to diffuse the bio-fluid 96 containing the cells 97 into the prosthetic trachea 20 using a bioreactor which may, for example, entail subjecting the bioreactor container 80 to specific environmental conditions to initiate or speed cell proliferation.

At another point prior to surgery, typically several hours in advance, one or more drugs 99 may be injected into the buffer solution 98. The membrane 94 separating that compartment 98 from the prosthetic trachea 20 is then compromised so that the prosthetic trachea 20 is soaked with the drug 99.

The outer walls of the bioreactor container 80 is preferably made of a medical-grade transparent polymer material. In some embodiments, the polymer material is polyethylene, and more specifically, high-grade polyethylene.

In some embodiments, one or both of the membranes 94, 95 is physically compromised to allow the bio-fluid 96 or the buffer solution 98 to enter the second compartment 92. In such embodiments, the membrane 94, 95 may be of the same material as the outer walls of the bioreactor container 80. The physical mechanism to breach the membrane may be a valve in the membrane 94, 95 or a re-sealable zip-locking slit in the membrane 94, 95.

In some embodiments, one or both of the membranes 94, 95 is chemically compromised to allow the bio-fluid 96 or the buffer solution 98 to enter the second compartment 92. In such embodiments, the membrane 94, 95 material may be a pH-sensitive polymer or a thermally-sensitive polymer. In some embodiments, the pH-sensitive polymer is a hydrogel, preferably having a pH sensitivity within the range of pH 4 to pH 10. In some embodiments, the thermally-sensitive polymer is a hydrogel, preferably with a transition temperature in the range of 0 to 50° C. When the material is a pH-sensitive polymer, the membrane 94, 95 is breached by adding one or more components to adjust the pH of the bio-fluid 96 or the buffer solution 98 to degrade the pH-sensitive polymer at the appropriate time. When the material is a thermally-sensitive polymer, the membrane 94, 95 is breached by changing the temperature of the bio-fluid 96 or the buffer solution 98 to degrade the thermally-sensitive polymer at the appropriate time.

Among the advantages of the integrated prosthetic/container single unit is the ability to personalized the prosthetic implant with specific cells 97 and drugs 99 determined by a physician to be most beneficial for a particular patient in addition to the ability to provide a personalized or anatomically customized prosthetic as previously described. Without limitation, other benefits include ease of storage and an ability to extend the shelf life of the prosthetic (illustrated as a textile trachea but which, as already described elsewhere herein, may be any other predetermined anatomical or geometric shape for the type of tissue scaffold desired).

Although the bioreactor container 80 is shown in FIG. 9 with the compartments 91, 92, 93 is a side-by-side configuration, the bioreactor container 80 may alternatively be arranged in a vertical stack. In such an arrangement, the second compartment 92 containing the prosthetic trachea 20 is located at the bottom of the bioreactor container 80, with the first compartment 91 and the third compartment 93 being located above the second compartment 92. The first compartment 91 and the third compartment 93 may be located side-by-side of each other or the first compartment 91 may be located above the third compartment 93, with the second compartment 92 on the bottom.

Historically, in narrow shuttle graft weaving, each region of weaving uses its own shuttle: one for the aorta and one for each iliac. Using this methodology to make a bifurcated graft, three shuttles are necessary. If you carried out this method further, to make a trifurcated graft, four shuttles are necessary if the split happens at the same location and five shuttles are needed if the splits are offset. To make a quadfurcated graft using this method, at least five shuttles are needed to make a graft that splits at the same region and six to seven shuttles are needed if the splits are offset.

Because most shuttle looms only have a capacity of four shuttles, this can limit their capacity to be used in the manufacture of complex shapes, such as four lumen articles, as conventional methods requires one shuttle per region per thickness.

However, exemplary embodiments employ a more efficient use of shuttle motion to allow shuttles to be used in more than one region to create woven seamless tubular graft fabric structures that splits into three, four, or more lumens, while accomplishing it with no more than the same number of shuttles as the total number of lumens. While primarily described herein with respect to a four lumen article on a four shuttle loom, it will be appreciated that the principles of the disclosure may be employed on a loom with more shuttles, and that it is possible to split into as many lumens as there are shuttles.

In one embodiment, a multi-lumen article is woven in the form of a quadfurcated vascular graft. The graft is woven on a narrow shuttle loom with four shuttles and sixteen harnesses, in which there are four sets of four harnesses for each of the four legs, the graft having a single wide tube for connecting to a primary vessel, such as the aorta, splitting once into two legs, in which each of those legs is itself split into another set of two legs.

Figure 10:
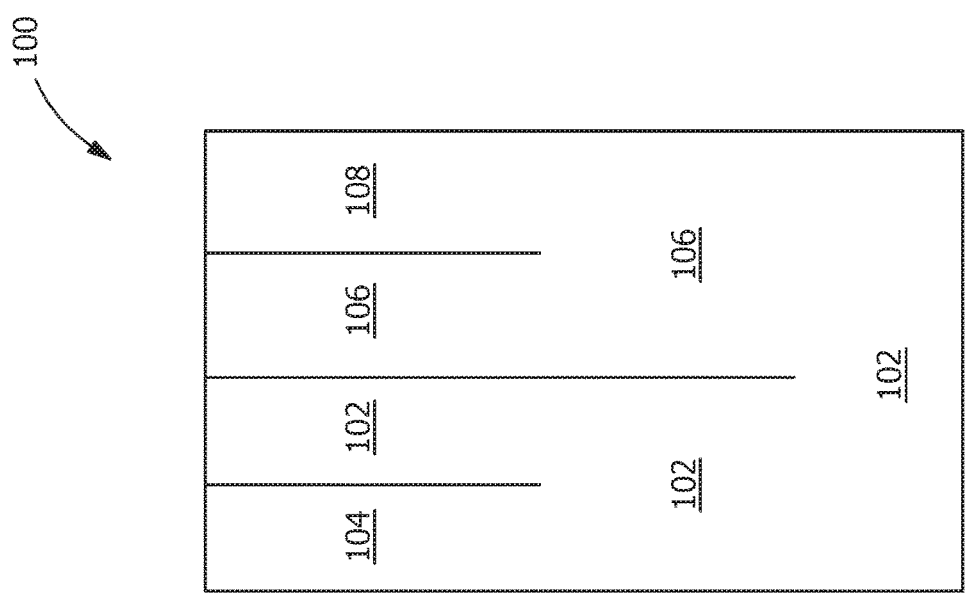
FIG. 10 schematically shows a shuttle path of a quadfurcated vascular graft having equal leg lengths in an embodiment of the present disclosure.

Referring to FIG. 10, s1 102 and s2 104 are on the left of the shuttle path 100; s3 106 and s4 108 are on the right in the shuttle path 100. In order to keep shuttles 102, 104, 106, 108 from crossing, the four leg regions move such that the inner legs weave first, face and back, then the outer legs. Thus, in the four leg regions shown in FIG. 10, the shuttle action is, starting s1 102 and s2 104 left and s3 106 and s4 108 right: s1 102→←; s2 104→←; s3 106→←; and s4 108→←. This embodiment was woven with a 1/140 PET warp under tension.

Figure 12:
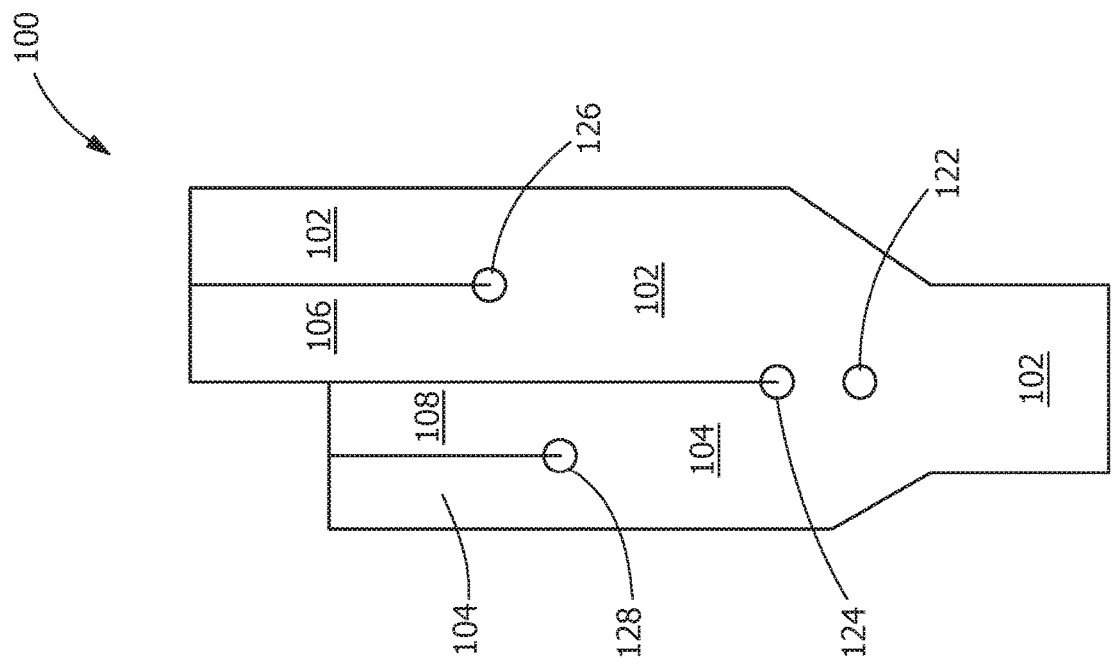
FIG. 12 schematically shows a shuttle path of the quadfurcated vascular graft of FIG. 11.
Figure 11:
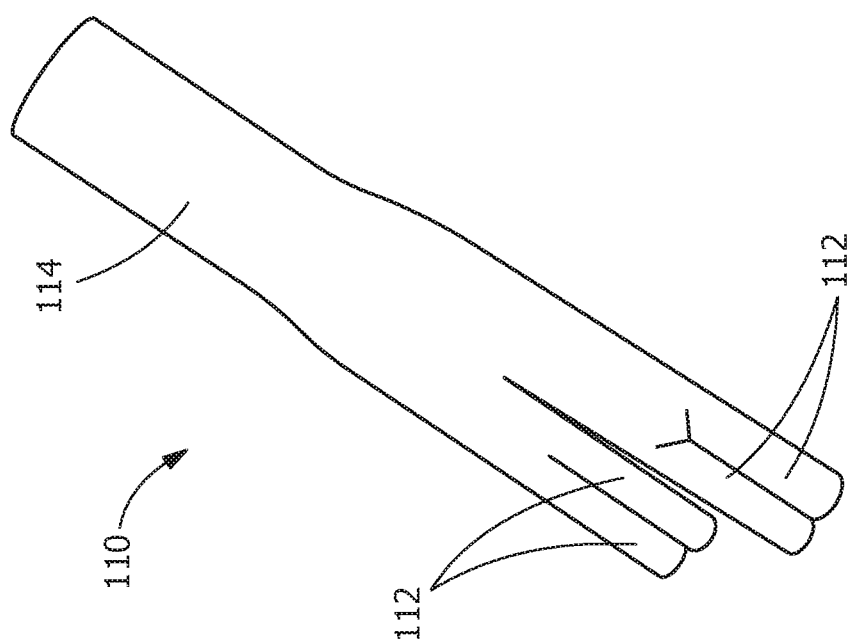
FIG. 11 schematically shows a quadfurcated vascular graft having legs of different lengths in an embodiment of the present disclosure.
Figure 14:
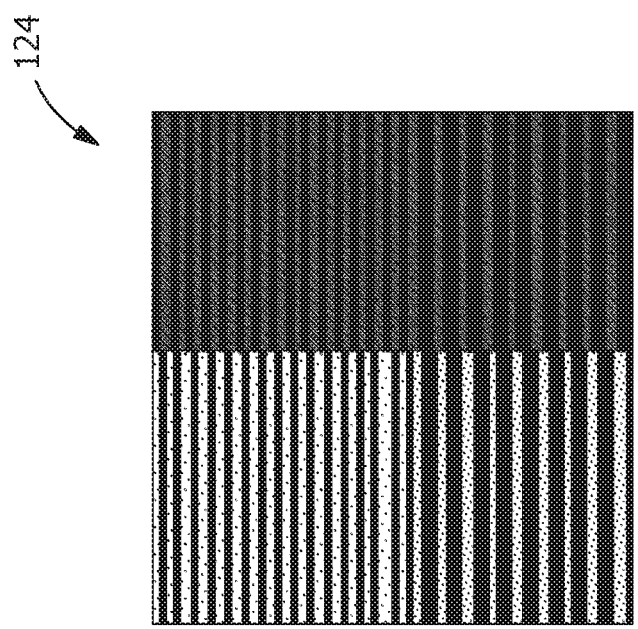
FIG. 14 schematically shows a layout for region 124 of FIG. 12.
Figure 13:
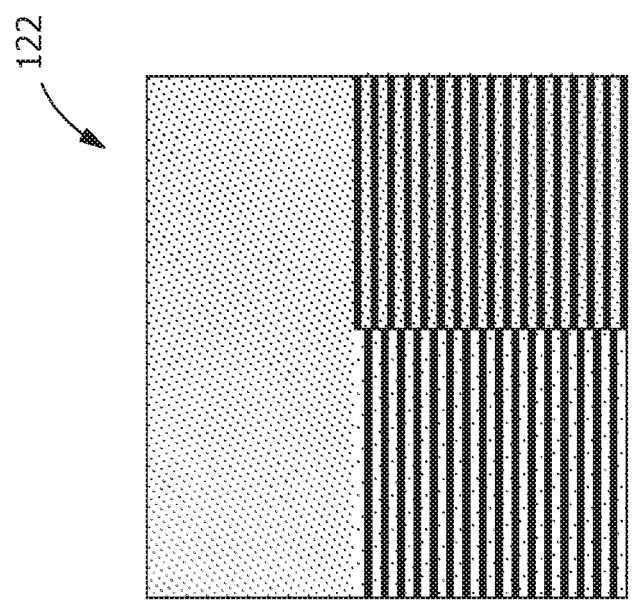
FIG. 13 schematically shows a layout for region 122 of FIG. 12.
Figure 16:
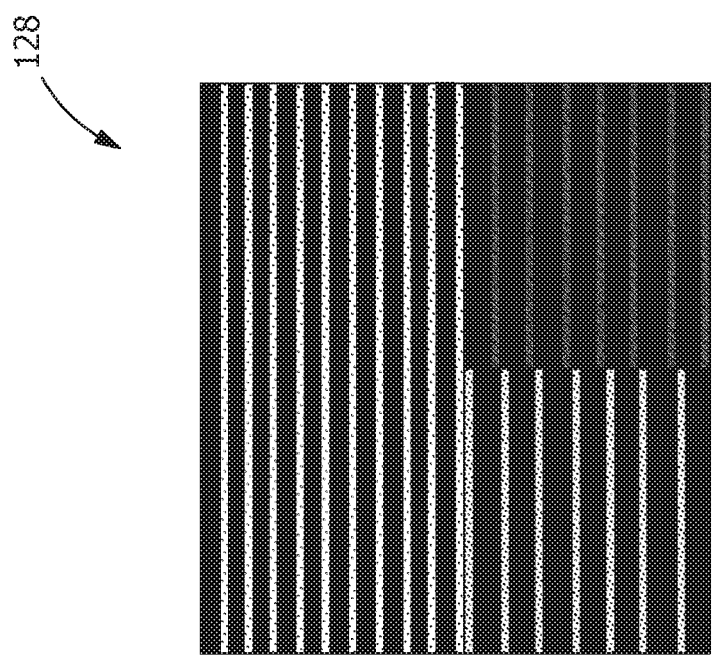
FIG. 16 schematically shows a layout for region 128 of FIG. 12.
Figure 15:
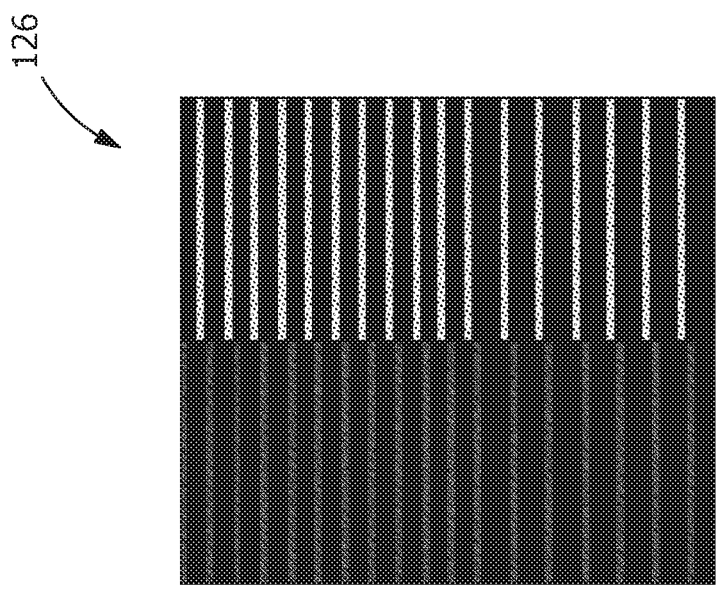
FIG. 15 schematically shows a layout for region 126 of FIG. 12.

Alternatively, a quadfurcated vascular graft 110 may be formed having legs 112 of different lengths, as shown in FIG. 11. A two dimensional illustration of the shuttle path 100 for the graft 110 of FIG. 11 is shown in FIG. 12. When the aortic region 114 is a complete tube, as shown in FIG. 11, all four sets of harnesses are weaving a plain tube together on s2 104. When the lumen splits into two, s2 104 continues weaving on the left hand lumen using the first and second sets of harnesses and s1 102 begins to weave the right hand lumen using the third and fourth sets of harnesses. When the left lumen splits into two, s2 104 weaves the most left lumen using s1 102 on the first harness set and s3 106 starts weaving the second harness set. When the right lumen splits, s4 108 begins weaving the third set of harnesses and s2 104 weaves the fourth harness set. Weaving occurs in pairs of picks, an out and back, for each leg.

In one embodiment, the article is woven with 1/40/27/12z PET at 150 picks per inch and 255 ends per inch on the face of the fabric and the weave is a plain weave tube.

By way of further illustration, the regions 122, 124, 126, and 128 of FIG. 12 are further illustrated by way of the layout for each of those regions as shown in FIG. 13, FIG. 14, FIG. 15, and FIG. 16, respectively, for use in conjunction with a jacquard loom. The black areas in the layouts of FIG. 13 through FIG. 16 represent a "cut". The jacquard weaving process facilitates control between the structural relationship of the horizontal and vertical intersections of warp and fill yarn, with a predetermined quill placement controlling the fill material being thrown across the shed. By weaving a continuous lumen that divides naturally, clot formation is reduced by reducing turbulent areas of the vascular graft 110, such as at seams that occur in conventional methods of sewing together multiple bifurcated articles. Manufacturing is also simplified because of the reduction in the number of parts necessary for the vascular graft 110.

Figure 17:
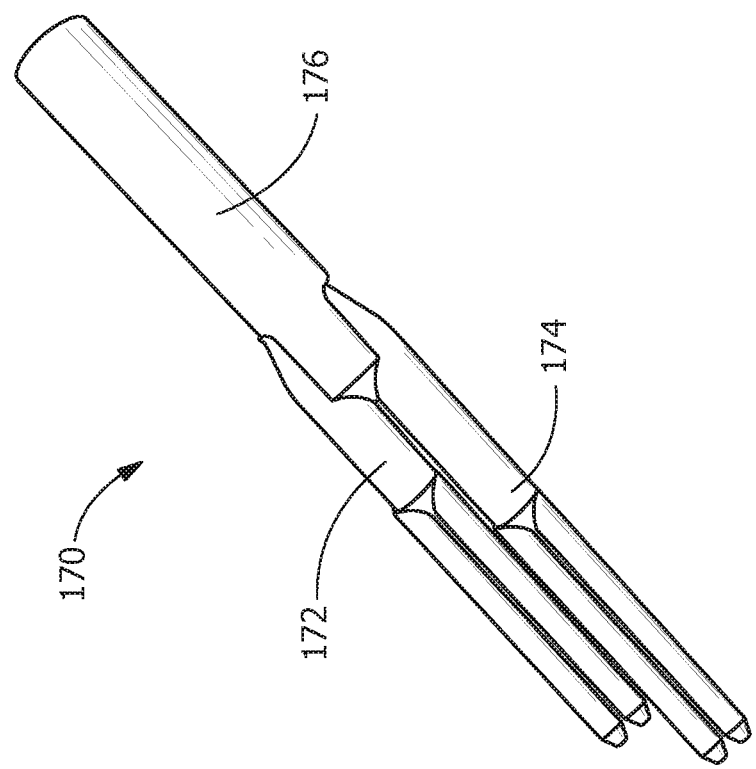
FIG. 17 schematically shows a mandrel for the quadfurcated vascular graft of FIG. 11.

In some embodiments, the lumens are sized to a special mandrel 170 that may be assembled inside the lumen, such as shown in FIG. 17 for the vascular graft 110 of FIG. 11. The mandrel is in three pieces: a left bifurcate piece 172, a right bifurcate piece 174, and an aortic piece 176. The left bifurcate piece 172 and the right bifurcate piece 174 are placed first. The aortic piece 176 is pegged to fit between the leg pieces 172, 174 when placed into the aortic region 114 of the lumen. The sizes of the lumen may be of any desired diameters, which may vary depending upon the particular device being created and which, even when used as vascular grafts 110, may still vary depending upon age, gender, and other anatomical characteristics of a particular patient. In one embodiment, the four quadfurcated lumens are each 8 mm in diameter, and the two bifurcated lumens are 16 mm in diameter, with a 24-mm diameter for the aortic region 114 of the lumen. Thus, as in this embodiment, it is possible for the diameter of the single lumen region to be narrower than the sum of the diameters of the furcated region.

Likewise, the length and distance to each of the relevant splits may vary, but in one embodiment the lumen is 12 cm in total length, with the aortic region 114 being about 3 cm, a taper out to 32-mm diameter occurring over the next 2 cm. The first split (from one to two lumens) occurs at a length of about 5 cm, with the left split into the first set of quadfurcated lumens occurring at about 7 cm, and the right split to fully quadfurcate at about 9 cm.

Once the mandrel 170 is assembled, the vascular graft 110 may be heat-set on the mandrel 170. The time and temperature to heat set the vascular graft 110 may vary depending on a variety of factors, but may generally be accomplished using elevated temperatures, such as, for example, 200 to 225° C. (392 to 437° F.), for short periods of time, such as, for example 5-12 minutes. Additionally or alternatively to the heat set, shape memory stent material may be sewn into the vascular graft 110 while on the mandrel 170 to aid in shape retention. The shape memory stent material may be memory wire sewn to the outside to give the fabric form its final shape.

As noted, exemplary embodiments provide a method for making as many furcations as the number of shuttles available. Thus, some embodiments result in trifurcated grafts, or even a bifurcated graft when only two shuttles are available, with the number of branches limited to the total number of shuttles available. Diameters may be different in every branch or they may be the same.

The variety of possible configurations is exemplified by FIG. 18A through FIG. 18F. The material used to form the tube of the vascular graft 110 may be any desired material including, but not limited to, PET, polypropylene, ultra-high-molecular-weight polyethylene (UHMWPE), nylon, PGA, PLA, poly-L-lactic acid (PLLA), or PGS. Additionally or alternatively, the woven prosthetic may include natural polymer fibers such as, but not limited to, collagen, fibronectin, hyaluronic acid, or a combination thereof. In another embodiment, a ratio of materials is selected to provide predetermined tissue compliance and/or biological properties. Based upon the material used to form the woven structure, the textile engineered prosthetic vascular graft 110 forms permanent hardware for a patient or an article of regenerative medicine. For example, permanent hardware may include non-resorbable materials or combinations of resorbable and non-resorbable materials, while articles of regenerative medicine may include scaffolds formed from resorbable materials, which are broken down after implantation.

Further, the prosthetic article may be woven with monofilament, multifilament, tape, or spun yarn, for example, and any style weave may be used for the base. While some embodiments use a plain weave, a twill, satin, basket, crepe, or any other weave may also or alternatively be employed.

In some embodiments, two different yarns may be employed for filling the lumens. In that case, the number of final branches possible is the number of shuttles divided by two. For example, a four shuttle loom is capable of making a bifurcate with two different picks where s1 and s2 are used for the aorta and the left leg and s3 and s4 are used for the right leg. Similarly, a six shuttle loom may make a trifurcated structure.

This method of dividing lumens is applicable to weaving prosthetic devices for a variety of tubular organic branching structures that may include, but are not limited to, arteries, veins, the trachea and bronchial branches, and bronchial tubes, for example. In some embodiments, the prosthetic trachea 20 described herein may be further split into multiple bronchial branches, with half as many branches as there are shuttles.

While described primarily with respect to woven prosthetics, the principles of the disclosure may also be extended to other woven devices where furcations are desired and may include, for example, carbon fiber or fiberglass structures for tubular preforms that may be set to shape or for created exterior support structures for concrete formwork, where the furcated tubes are filled with concrete to build architectural elements.

Additionally or alternatively, for embodiments in which the woven article is a prosthetic, the prosthetic may be seeded or incubated with biological cells 97 and/or drugs 99 such as, for example, with the bioreactor container 80 of FIG. 8 and FIG. 9. Suitable drugs 99 may include release agents. Suitable release agents may include, for example, trophic agents; proteins; peptides; cell growth agents; filler oxides; compounds that promote cellular attachment, cellular differentiation, regeneration, and/or tissue colonization; or a combination thereof. The release agents are released through any suitable release method, including, but not limited to, coating release, controlled coating release, fiber degradation, or a combination thereof. For example, the prosthetic may be a vascular graft 110 formed from degradable fibers including filler oxides or other release agents that are released as the fibers degrade. Suitable biological cells 97 may include, but are not limited to, progenitor cells, autologous cells, allogenic cells, mesenchymal progenitor cells, stem cells, or a combination thereof. The progenitor cells and/or release agents facilitate integration of the prosthetic and/or prosthetic functioning similar or substantially similar to that of the biological organ being reconstituted and/or replaced.

In one embodiment, after exposure of the prosthetic to the biological cells 97 and/or the drug 99, the prosthetic is incubated in a bioreactor container 80 prior to implantation. In another embodiment, the prosthetic includes additives that may include, but are not limited to, fluorescence compounds, radio opaque compounds, anti-bacterial compounds, growth hormones, conductive compounds, ceramic compounds, metallic compounds, oxygen-sensing compounds, radioactive compounds, hormones, cytokines, or combinations thereof. In a further embodiment, the prosthetic includes addition anatomical and non-anatomical features such as, for example, a feature configured to facilitate post-surgical tracheotomy, pores, dimples, hairs, patterned embossing, or a combination thereof.

In some embodiments involving incubation in a bioreactor container 80, the prosthetic may be integrated within a bioreactor container 80 such that the bioreactor container 80 and the prosthetic are part of a single, individualized unit to provide an off-the-shelf, but still fully customizable, tissue scaffold.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of manufacturing a furcated textile article comprising:
    weaving a continuous tube with a shuttle loom;
    furcating the continuous tube into N portions, wherein N is at least two, where N is equal to a shuttle capacity of the shuttle loom;
    forming at least one band of increased thickness formed over a portion of the continuous tube, wherein the at least one band of increased thickness forms a biomimetic surface; and
    wherein the band is C-shaped.

2. The method of claim 1, where N is at least three.

3. The method of claim 1, where N is at least four.

4. The method of claim 1, wherein the furcated textile article is a vascular graft.

5. The method of claim 1, wherein weaving the continuous tube comprises forming a body portion and a bifurcated portion extending from the body portion.

6. The method of claim 1, wherein forming the band includes a six-step shuttle sequence comprising:
(1) moving from face of the fabric left to face of the fabric right to weave a face of the fabric;
(2) moving from face of the fabric right to back of the fabric left to weave a back fabric right;
(3) moving from back of the fabric left to back of the fabric right to weave the back fabric right;
(4) moving from back of the fabric right to face of the fabric left to weave the face of the fabric;
(5) moving from face of the fabric left to back of the fabric right to weave a back fabric left; and
(6) moving from back of the fabric right to back of the fabric left to weave the back fabric left.

7. The method of claim 1, wherein forming the band includes a four-step shuttle sequence comprising:
(1) moving from face of the fabric left to face of the fabric right to weave a face of the fabric;
(2) moving from face of the fabric right to face of the fabric left to weave the face of the fabric;
(3) moving from face of the fabric left to back of the fabric right to weave a back of the fabric; and
(4) moving from back of the fabric right to back of the fabric left to weave the back of the fabric.

8. The method of claim 1, wherein the textile engineered prosthetic comprises a prosthetic trachea.

9. The method of claim 1, wherein the band extends around ⅓ to ⅔ of an outer diameter of the continuous tube.

10. The furcated textile article of claim 1, wherein the furcated textile article is a prosthetic trachea.

11. The method of claim 1, wherein the at least one band of increased thickness is integral to the continuous tube.

12. The method of claim 9, wherein the at least one band of increased thickness is integral to the continuous tube.

13. The method of claim 1, wherein the thickness is measured in a radial direction of the continuous tube.

* * * * *